United States Patent [19]

Lindahl et al.

[11] Patent Number: 4,824,678

[45] Date of Patent: Apr. 25, 1989

[54] CONTROLLED-RELEASE MEDICAL PREPARATIONS

[75] Inventors: Åke R. Lindahl, Skurup; Bo M. Ekman, Malmö both of Sweden

[73] Assignee: Aktiebolaget Leo, Helsingborg, Sweden

[21] Appl. No.: 772,779

[22] Filed: Sep. 5, 1985

Related U.S. Application Data

[63] Continuation-in-part of Ser. No. 647,928, Sep. 5, 1984, Pat. No. 4,557,925, which is a continuation of Ser. No. 396,391, Jul. 8, 1982, abandoned.

[30] Foreign Application Priority Data

Sep. 6, 1984 [SE] Sweden ................................ 8404467

[51] Int. Cl.$^4$ .......................... A61K 9/44; A61K 9/32; A61K 9/22
[52] U.S. Cl. .................................................... 424/473
[58] Field of Search .................................. 424/19–22, 424/32–33, 35, 473, 482,

[56] References Cited

U.S. PATENT DOCUMENTS

| | | | |
|---|---|---|---|
| 2,887,438 | 5/1959 | Cooper et al. | 167/82 |
| 3,538,214 | 11/1970 | Polli | 424/19 |
| 4,557,925 | 12/1985 | Lindahl et al. | 424/19 |
| 4,769,027 | 9/1988 | Baker et al. | 424/473 |

FOREIGN PATENT DOCUMENTS 0013131 12/1979 European Pat. Off. .

OTHER PUBLICATIONS

Goran Kallstrand and Bo Ekman, "Membrane-Coated Tablets: A System for the Controlled Release of Drugs", *Journal of Pharmaceutical Sciences*, vol. 72, No. 7 (Jul. 1983), pp. 772–775.

L. Bonnet "Process for Making Microporous Membranes", *Research Disclosure*, vol. 135, pp. 74–75 (Jul. 1975).

*Primary Examiner*—Shep K. Rose
*Attorney, Agent, or Firm*—Pravel, Gambrell, Hewitt, Kimball & Krieger

[57] ABSTRACT

The present invention concerns a novel pharmaceutical preparation having a biphasic release pattern. The preparation comprises a tablet core containing a drug. The tablet is coated with a coating essentially consisting of a film-forming water-insoluble polymer having fine water soluble particles randomly distributed therein. The fine particles include a drug active substance, which is the same as the drug in the core. The drug active substance in the particles may also be different from the one in the tablet core.

22 Claims, No Drawings

CONTROLLED-RELEASE MEDICAL PREPARATIONS

This is a continuation-in-part application of U.S. application Ser. No. 647,928 filed Sept. 5, 1984 (issued Dec. 10, 1985 as U.S. Pat. No. 4,557,925) which in turn is a continuation of U.S. application Ser. No. 396,391 filed July 8, 1982 (now abandoned).

The present invention relates to an oral pharmaceutical controlled-release preparation which has a biphasic release profile of pharmacologically active agent(s).

PRIOR ART

Oral preparations having a biphasic release profile of the active drug(s) are previously known.

Common medical preparations disclosing a biphasic release profile of one or more pharmacologically active agents include a tablet core from which the active substance is released and a surrounding coating from which the same or a different substance is released. The surrounding coating is applied in a conventional coating step. The release from the core may occur at a slow, moderate or rapid rate.

An oral preparation of this type is disclosed in e.g. the U.S. Pat. No. 3,538,214. This patent discloses a pharmaceutical preparation consisting of a tablet core comprising a medicament, which is soluble in gastrointestinal fluids, and a coating on said core. The coating consists of a polymer substance which remains substantially intact and insoluble in the gastro-intestinal fluids. Fine particles of a readily water-soluble substance are randomly distributed in the coating. Furthermore, it is disclosed in the patent that the preparation can be provided with an additional coating which i.e. may contain another pharmacologically active substance.

Another preparation characterized by biphasic release profile is disclosed in the European patent application No. 13131. From the specification and disclosed examples it is obvious that this kind of preparation includes an active ingredient incorporated in a controlled release matrix comprising a higher aliphatic alcohol and a hydrated water soluble hydroxy alkyl cellulose. On this matrix, which slowly releases the active ingredient is applied a standard film coating solution, in which a second active agent is dissolved or suspended.

As will be obvious from the following description and examples the present invention is concerned with a different type of preparation, wherein the slow release of the active ingredient included in the core is obtained by the dissolution rate limiting properties of special type of film surrounding the core and not as according to the European application by the rate-limiting properties of the core matrix.

OBJECTS OF THE INVENTION

It is an object of the present invention to provide a novel pharmaceutical tablet having a biphasic release of the drug(s).

A second object of the present invention is to provide a method according to which such tablets can be prepared using one single coating process.

A third object is to provide a simple and useful method of obtaining a wide variety of biphasic release patterns.

A forth object is to provide a medical preparation which can offer variable release patterns for different drugs or drug combinations.

SUMMARY OF THE INVENTION

The present invention concerns a controlled-release coated pharmaceutical preparation comprising a drug tablet and a coating applied thereon, wherein the coating essentially consists of a film-forming polymer which is insoluble in water and gastrointestinal fluids and a water-soluble pore-creating material being randomly distributed in said polymer. The preparation is characterized in that the pore-creating material partially or totally consists of a drug active substance in sufficient amounts to produce a pharmacological or therapeutical effect.

The present invention also provides a method of preparing this controlled-release preparation comprising the steps of dissolving the said polymer in a solvent, preparing a suspension or solution of the pore-creating material, providing a pharmaceutical tablet combining the suspension or solution of pore-creating material and solution of the polymer to form a coating fluid, applying the coating fluid in the form of a solution or suspension to the tablet and drying the coating fluid on the tablet to provide a polymer-coated tablet having water-soluble pore-creating material randomly distributed within the polymer.

The preparation according to the invention is advantageous for two principally different controlled-release embodiments.

One preferred embodiment of the invention concerns medical preparations of at least two different pharmacologically or drug active substances which should be provided in combination. According to this embodiment the drug in the core may be e.g. potassium chloride and the drug active substance included in the pore-creating material may be an instant release diuretics such as metolazone, clopamide, ethacrynic acid, hydroflumethiazide, methylchlothiazide, quinethazone, trichloromethiazide, chlorothiazide, chlorothalidone, cyclothiazide, furosemide, hydrochlorothiazide, polythiazide, bendroflumethiazide, cyclopenthiazide, mefruside, and bumetanide.

Another example is a core containing theophylline or a theophylline salt such as ethylene diamine theophyllinate or choline theophyllinate, and the pore creating material being a beta-2-stimulant such as salbutamol or terbutaline.

In this connection it should be pointed out that the U.S. Pat. No. 3,538,214 discussed previously discloses of the combination potassium chloride and hydrochlorothiazide, but in this preparation the hydrochlorothiazide is present in an additional overcoating (cf Example II). Consequently, the method to combine two different active substances in one and the same tablet is much more complicated according to the method known from the U.S. patent than according to the present invention, and the disclosure of the U.S. patent actually teaches away from the present invention.

According to another embodiment the pore-creating material includes the same drug active agent as the core. Such a formulation provides a rapid release giving rise to initially effective plasma levels which are then maintained by the controlled release action of the preparation. Example of a drug suitable for such a preparation is phenylpropanol amine (PPA) which is used i.a. as a nasal and sinus decongestant. It is also widely used as an appetite suppressant. CNS stimulation caused by PPA, if used in the late part of the day, may interfere with sleep at night. An ideal formulation of PPA would produce effective plasma concentrations during daytime, i.e. for 16 hours, while it gives low or negligible plasma concentrations during night.

Other interesting fields where the same active substance is present in the core and as (part of) the pore-creating material in the coating are penicillins, cephalosporines, benzdiazepines, calcium antagonists, e.g. diltiazem and short-acting hypnotics.

The release pattern of the active substance from the tablet core may be adapted to fit various requirements by varying the ratio of pore-creating material versus coating polymer, the combination of pore-creating substances and the coating thickness. It is often preferred to choose the parameters, which give the coating such properties that a constant, i.e. zero order, release of the active drug in the core is obtained.

DETAILED DESCRIPTION OF THE INVENTION

The filmforming polymeric substances used for the coating mixtures according to the present invention are pharmaceutically acceptable filmforming polymers which are substantially water-insoluble but soluble in organic solvents, e.g. ketones. Examples of such substances are cellulose derivatives, acrylic polymers, and other high molecule polymers such as ethylcellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polyester, coumarone-indene polymer, polybutadiene, vinyl chloride-vinyl acetate copolymer, ethylene-vinyl acetate copolymer and vinyl chloridepropylene-vinyl acetate terpolymer.

The polymeric membranes applied may also comprise a plasticizer. As examples of plasticizers may be mentioned triacetin, acetylated monoglyceride, rape oil, olive oil, sesame oil, acetyltributyl citrate, acetyltriethyl citrate glycerin, sorbitol, diethyl oxalate, diethyl malate, diethylfumarate, diethyl succinate, diethyl malonate, dioctylphthalate, dibutyl sebacetate, triethyl citrate, tributyl-citrate, glycerol tributyrate, polyethylene glycol, propylene glycol, and mixtures of the above. Especially preferred are plasticizers such as acetyl tributyl citrate, polyethylene glycol, blown castor oil and glyceryl triacetate.

The amount of plasticizer may vary between 0.1 and 4% weight by weight of the coating fluid.

The pore-creating material according to the present invention can be any substance which gives the desired pharmacological effect, is pharmaceutically acceptable and fulfils the following requirements:
(A) When coated in suspension form:
  (1) It must be soluble in water (gastro-intestinal fluids).
  (2) It must be essentially insoluble in the organic solvents used in the coating process, e.g. in acetone, methyl ethyl ketone.
  (3) It should have a particle size of 0.5–100 $\mu$m.
(B) When coated in solution form:
  (1) It must be soluble in water (gastro-intestinal fluids).
  (2) It must be essentially soluble in the organic solvents used in the coating process, e.g. in acetone, methyl ethyl ketone.
  (3) It should have a particle size of 0.5–100 $\mu$m provided that in (A) and (B) above the pore-creating material does not include (pharmacologically inactive amounts of) calcium carbonate, calcium phosphates, magnesium citrate, magnesium oxide, sodium bicarbonate, potassium bicarbonate, tetraethanolamine, propionic acid, sorbic acid, salicylic acid and cellulose acetate phthalate, potassium chloride or sodium chloride.

According to the present invention a wide variety of coatings can be used. Depending on the manufacturing process and the fact that, when in the living body, the coating is affected by several factors (influence of different pH, different enzymes motility of the intestines) it is obvious that some filmforming polymers are more suitable than others. Thus it has been found that a copolymer of vinyl acetate and vinyl chloride gives good results. Another especially preferred polymer is a terpolymer containing 80–95% weight per weight of polyvinylchloride, 1–19% weight per weight polyvinyl acetate and 1–10% weight per weight of polyvinyl alcohol.

The amount of pore-creating material which consists of the drug active substance depends on the level of the substance initially required. In order to get the desired slow release pattern of the drug in the core it may sometimes be required that pore-creating material includes additional amounts of water-soluble material, which meet with the requirements mentioned above and which is pharmaceutically acceptable and pharmacologically essentially inactive at the amounts used. The weight ratio total amount pore-creating material to polymer depends on the polymer chosen and the release pattern desired. The additional inactive material, which if required is included in the pore-creating material, may e.g. consist of sucrose, polyvinylpyrrolidone or a polyethylene glycol. If a polyvinyl acetate copolymer or a polyvinyl acetate-polyvinyl chloride-polyvinyl alcohol terpolymer is used it is suitable that the ratio of total pore-creating material to polymer varies between 0.1 and 20, preferably 1 and 5 and especially 1.5 and 3.

The coating fluid is produced in the following manner:

A polymer which preferably could be a terpolymer containing (w/w%) 80–95% PVC (polyvinylchloride), 1–19% PVAC (polyvinylacetate), and 1–10% PVOH (polyvinylalcohol) is dissolved in a solvent, e.g. acetone, methylenechloride, methylethylketone, or mixtures of acetone and ethanol, acetone and methylenechloride, or the like.

The pore-creating particles including drug active substance and optionally additional inactive substance are ground either by dry milling in a ball mill or by wet-milling in a glass bead milling device to a defined particle size, preferably between 0.5 $\mu$m and 100 $\mu$m. The particles are dispersed in solvents or mixtures of solvents, such as those previously mentioned, and mixed with the polymer solution to form the coating fluid.

Depending on the size and area of the tablet the coating weight may vary between 10 and 170 mg per tablet and the coating thickness may vary between 25 and 300 $\mu$m, preferably between 50 and 200 $\mu$m.

The invention is further illustrated by but not limited to the following examples, wherein the examples 1–3 disclose preparations in which the same active drug is present in the core and in the coating.

EXAMPLE 1

Phenylpropanolamine 75 mg

| Tablet: | |
|---|---|
| Phenylpropanolamine* | 50 mg |
| Polyethylenoxide 6000 | 60 mg |
| Sucrose M sieved | 72.6 mg |
| Polyvinylpyrrolidone | 5 mg |
| Magnesiumstearate | 2 mg |
| Ethanol | |

The ingredients were mixed except for the Mg-stearate; moistened with ethanol and dried. After drying the powder was mixed with Mg-stearate and the mixture was compressed to tablets.

| Coating suspensions: | | | |
|---|---|---|---|
| | A | B | C |
| Filmforming terpolymer | 7 mg | 10 mg | 14 mg |
| Acetyltributyl citrate | 2.23 mg | 2.23 mg | 2.23 mg |
| Blown castor oil | 1.67 mg | 1.67 mg | 1.67 mg |
| Phenylpropanolamine | 25 mg | 25 mg | 25 mg |
| Polyvinylpyrrolidone | 1.34 mg | 1.34 mg | 1.34 mg |
| Acetone | 526 mg | 526 mg | 526 mg |

Sieved phenylpropanolamine was dispersed in acetone solutions of the polymer and plasticizer. The suspensions were coated on to the tablets in a coating pan. The filmforming polymer used in this example consisted of a terpolymer of $(PVC)M$, $(PVAC)N$, $(PVOH)O$, wherein PVC is polyvinylchloride, PVAC is polyvinylacetate and PVOH is polyvinylalcohol. $M=31$, $N=1$ and $O=2$.

The phenylpropanolamine diffusion from the three types of tablets having different amounts of polymer in the coating was followed by using the paddle method described in the U.S. Pharmacopeia, 19th rev., Mack Publishing Co., Easton, Pa., 1975, p. 651 (=USP XX).

As can be seen from the accompanying figure all three types of tablets give a rapid release of the drug during the first hour. After that a slow release dissolution over a long period of time can be obtained. The rate of the slow release can be varied by changing the amount of polymer.

EXAMPLE 2

| Tablet: | |
|---|---|
| Cefaclorum | 340 mg |
| Avicel PH | 20 mg |
| Powdered sucrose H | 143 mg |
| Aerosil | 13 mg |
| Stearin talc 50% | 33 mg |

The ingredients were mixed in a double-cone mixer and compressed to tablets.

| Coating: | |
|---|---|
| Cefaclorum (sieved) | 60 mg |
| Filmforming polymer | 14.3 mg |
| Acetyltributyl citrate | 2.7 mg |
| Blown castor oil | 2.2 mg |
| Polyvinyl pyrrolidone | 1.9 mg |
| Acetone | |

The filmforming polymer consisted of a $(PVC)M$, $(PVAC)N$, $(PVOH)O$ terpolymer, wherein $M=100$, $N=1$ and $O=8$.

EXAMPLE 3

Nitrazepame 6 mg

| Tablet: | |
|---|---|
| Nitrazepame | 4 mg |
| Powdered sucrose | 120 mg |
| Polyethylene oxide 6000 | 110 mg |
| Polyvinylpyrrolidone | 5 mg |
| Magnesium stearate | 2 mg |

The ingredients except for the Mg-stearate were mixed and moistened with ethanol. After drying Mg-stearate was added and the powder was compressed to tablets.

| Coating: | |
|---|---|
| Filmforming polymer according to Example 1 | 9.8 mg |
| Acetyltributyl citrate | 1.87 mg |
| Blown castor oil | 1.40 mg |
| Nitrazepam (sieved) | 2 mg |
| Micronized sucrose | 23 mg |
| Acetone | 530 mg |

EXAMPLE 4

The following example discloses a preparation, in which different drug active substances are present in the core and in the coating.

The tablet core contained 1 g potassium chloride.

The coating suspension had the following composition:

| | |
|---|---|
| Filmforming polymer according to Example 1 | 180 g |
| Micronzied powdered sucrose (particle size 1-10 μm) | 409 g |
| Acetyl tributyl citrate | 40.9 g |
| Blown castor oil | 31.2 g |
| Bendroflumethiazide | 34.0 g |
| Acetone ad | 4400 g |

The coating process is performed in a coating pan and the coating fluid is sprayed onto the tablets with an airless spray-coating device. Five thousand tablets are coated and the average membrane weight is 60 mg per tablet.

EXAMPLE 5

The procedure according to Example 1 was followed but nitrocellulose was used as filmforming substance instead of the terpolymer.

EXAMPLE 6

The procedure according to Example 1 was followed but cellulose acetate was used as filmforming substance instead of the terpolymer.

What is claimed is:

1. A controlled-release pharmaceutical preparation having a biphasic release profile, comprising; a drug tablet core and a coating applied thereon, said coating comprising a film-forming polymer which is insoluble in water and gastro-intestinal fluids and a water-soluble pore-creating material containing a therapeutically effective amount of a drug active substance, said pore-creating material being randomly distributed in said polymer.

2. The preparation of claim 1 wherein the pore-creating material contains a drug active substance different from that of the drug core.

3. The preparation of claim 1 wherein the drug active substance in the pore-creating material is the same substance as that present in the drug core.

4. The preparation of claim 1 wherein the pore-creating material further includes a substance, which is soluble in water and gastro-intestinal fluids and is essentially therapeutically inactive in the amount used, said amount being sufficient to give a preselected release profile.

5. The preparation of claim 2, wherein the film forming polymer is a terpolymer of polyvinylchloride, polyvinylacetate and polyvinylalcohol.

6. The preparation of claim 5, wherein the drug in the core is potassium chloride and the drug active substance included in the pore-creating material is an instant release diuretic.

7. The preparation of claim 5, wherein the drug in the core is theophylline or a theophylline salt and the drug active substance included in the pore-creating material is a beta-2-stimulant.

8. The preparation of claim 3, wherein the film forming polymer is a terpolymer of polyvinylchloride, polyvinylacetate and polyvinylalcohol.

9. The preparation of claim 8, wherein the drug active substance is phenylpropanolamine.

10. The preparation of claim 8, wherein the drug active substance is a hypnotic.

11. The preparation of claim 8, wherein the drug active substance is an antibiotic.

12. The preparation of claim 8, wherein the drug active substance is a tranquilizer.

13. The preparation of claim 2, wherein the film-forming polymer is selected from a group consisting of cellulose derivatives, acrylic polymers and vinylpolymers.

14. The preparation of claim 13, wherein the drug in the core is potassium chloride and the drug active substance included in the pore-creating material is an instant release diuretic.

15. The preparation of claim 13, wherein wherein the drug in the core is theophylline or a theophylline salt and the drug active substance included in the pore-creating material is a beta-2-stimulant.

16. The preparation of claim 3, wherein the film-forming polymer is selected from a group consisting of cellulose derivatives, acrylic polymers and vinylpolymers.

17. The preparation of claim 16, wherein wherein the drug active substance is phenylpropanolamine.

18. The preparation of claim 16, wherein wherein the drug active substance is a hypnotic.

19. The preparation of claim 16, wherein wherein the drug active substance is an antibiotic.

20. The preparation of claim 16, wherein wherein the drug active substance is a tranquilizer.

21. The preparation of claim 16, wherein the film-forming polymer is nitrocellulose and the drug active substance is phenylpropanolamine.

22. The preparation of claim 16, wherein the film-forming polymer is cellulose acetate and the drug active substance is phenylpropanolamine.

* * * * *